United States Patent [19]

Wentz

[11] Patent Number: 5,297,443
[45] Date of Patent: Mar. 29, 1994

[54] FLEXIBLE POSITIONING APPENDAGE

[76] Inventor: John D. Wentz, 369 Washington Ave., Apt. 2B, Brooklyn, N.Y. 11238

[21] Appl. No.: 909,960

[22] Filed: Jul. 7, 1992

[51] Int. Cl.$^5$ .................. G05G 11/00; B25J 18/06
[52] U.S. Cl. .................. 74/479 BF; 128/4; 446/27; 446/390; 901/21
[58] Field of Search .............. 74/479; 128/4; 446/27, 446/368, 390; 604/95; 901/21

[56] References Cited

U.S. PATENT DOCUMENTS

| | | | |
|---|---|---|---|
| 2,241,576 | 5/1941 | Barton | 46/152 |
| 3,060,972 | 8/1957 | Sheldon | 138/120 |
| 3,266,059 | 8/1966 | Stelle | 3/12.3 |
| 3,497,083 | 2/1970 | Anderson et al. | 214/1 |
| 3,546,961 | 12/1970 | Marton | 74/501 |
| 3,625,084 | 12/1971 | Siebert | 74/501 R |
| 4,393,728 | 7/1983 | Larson et al. | 74/469 |
| 4,489,826 | 12/1984 | Dubson | 198/812 |
| 4,494,417 | 1/1985 | Larson et al. | 74/469 |
| 4,551,061 | 11/1985 | Olenick | 414/735 |
| 4,566,843 | 1/1986 | Iwatsuka et al. | 414/680 |
| 4,683,773 | 8/1987 | Diamond | 74/479 |
| 4,712,969 | 12/1987 | Kimura | 414/730 |
| 4,753,222 | 6/1988 | Morishita | 128/4 |
| 4,787,369 | 11/1988 | Allred, III et al. | 128/4 |
| 5,005,558 | 4/1991 | Aomori | 128/4 |

FOREIGN PATENT DOCUMENTS

| | | | |
|---|---|---|---|
| 871786 | 10/1981 | U.S.S.R. | 128/4 |
| 1256955 | 9/1986 | U.S.S.R. | 901/21 |
| 1301701 | 4/1987 | U.S.S.R. | 901/21 |

Primary Examiner—Allan D. Herrmann
Attorney, Agent, or Firm—Eckert Seamans Cherin & Mellott

[57] ABSTRACT

A flexible appendage for use as a robot arm, controllable medical instrument, or simply a toy, has flexibly coupled segments defining an open lumen, and flanges protruding laterally of the axis. The flanges have passages for control lines spaced laterally from the axis. Each control line is fixed to a segment and can be pulled through the other segments from the proximal end. The control lines shorten a lateral side of the appendage to controllably bend it. Resilient couplings between the segments, leave open the lumen for passage of conduits or tools. The couplings can be helical springs wound with turns which abut at rest, such that the couplings elongate on the outside of a bend but do not compress on the inside, thereby maintaining the overall length of the appendage. The control lines are distributed around the axis, and can be arranged in ranks for controlling groups of the segments at different distances from the proximal end. The springs coupling proximal segments are more rigid than for distal segments, and the segments can be smaller and/or longitudinally shorter approaching the distal end.

17 Claims, 7 Drawing Sheets

FLEXIBLE POSITIONING APPENDAGE

BACKGROUND OF THE INVENTION

1. Field of the Invention

This invention relates to the field of elongated flexible structures having longitudinally operable tension or extension mechanisms spaced laterally of a central axis such that the flexible structures can be moved into a curved configuration by applying relatively more longitudinal tension or extension on one side of the axis than the other. More particularly, the invention concerns such a structure wherein a plurality of rigid segments, which are preferably coupled by closed helical springs that space flanged ends of the segments, are provided with control lines for exerting tension between a proximal end of the structure and at least one segment spaced from the proximal end.

2. Prior Art

Controllably bendable resilient structures are known, with segments coupled to define a longitudinal extension, and control lines passing through the segments at points spaced laterally of a central axis. An example is a toy snake which can be curved by shortening one of three laterally spaced control lines as disclosed in U.S. Pat. No. 2,241,576—Barton. The segments must be structured or connected to allow adjacent segments to tilt relative to one another along the axis. In Barton the segments have convex end surfaces which rest against one another at a point. The control lines extend freely through the segments from manually engageable finger rings (at the tail of the snake). The control lines can be pulled through the segments relative to their terminus at the last segment (the head) remote from the rings. By exerting unequal tension on the three laterally spaced control lines it is possible to cause the snake to bend, e.g., to rear its head. In so doing, the point at which adjacent segments contact one another moves laterally toward the inside of the curve. The segments are not connected mechanically to one another except by virtue of being strung like beads on the control lines.

Variations of the idea of curved segments and lateral control lines are disclosed, for example, in U.S. Pat. Nos. 4,393,728 and 4,494,417—both to Larson et al, in connection with a robot painting arm. U.S. Pat. No. 3,266,059—Stelle discloses a similar curved abutting surface in an articulated elbow joint between rigid members of a robot arm.

A variably flexible tether is disclosed in U.S. Pat. No. 3,546,961—Marton. A control cable passes through adjacent segments having concave and convex abutting surfaces. When tension is applied, the segments are pulled against one another and the device becomes relatively more rigid. When tension is released the device is flaccid. The convex/concave abutment between adjacent segments defines the degree of freedom of bending between the segments.

With non-compressible segments abutting at curved surfaces, such devices curve by tension on a control line at the lateral inside of the curve but do not become foreshortened longitudinally. This is because facing parts of the adjacent non-compressible segments remain in contact. The extent of possible bending is defined by the particular structure of the adjacent segments, i.e., by the extent of tilting available until portions of the segments spaced transversely from the longitudinal axis come into contact on the inside of the curve.

Arrangements which have compressible segments or a compressible element between non-compressible segments are relatively foreshortened when tension is applied and elongated when tension is released. Examples are shown in U.S. Pat. Nos. 3,060,972—Sheldon and 4,551,061—Olenick. In U.S. Pat. No. 4,712,969—Kimura, an extensible-retractable arm is provided wherein individually driven expansion-contraction elements are provided between each of the segments.

An important objective in a robot arm or similar controllable appendage is to accurately control the position of the distal end. A welding tool, spray head, grasping apparatus, video camera or any of various other structures can be mounted on the arm, and oriented or manipulated (e.g., applied to a workpiece) in a programmed manner. However, an arm comprising non-compressible segments with curved abutting faces is difficult to control accurately and to keep suitably stiff because there is no real connection between the adjacent segments. On the other hand, the longitudinal expansion and contraction inherent in resiliently coupled segments, which varies as tension is applied or changed to achieve a particular curve, makes accurate position programming difficult or impossible.

In U.S. Pat. Nos. 3,497,083—Anderson et al and 4,566,843—Iwatsuka et al, segments are coupled by universal joints between adjacent segments, defined by pivot axes oriented at right angles. These joints are non-compressible, but are heavy, complicated and expensive. Additionally, the joint structures eliminate the potential of an open lumen along the central axis of the arm, for passage of fluid lines and/or electrical lines, or at least substantially occlude the available space for such lines.

Assuming the flexible structure is applied to a device for positioning a free distal end, for example carrying a tool, the load to be borne by segments disposed closer to the proximal end is greater than the load for segments at the distal end because the proximal segments must carry the weight of the distal segments. Anderson and Iwatsuka use progressively smaller segments or groups of segments proceeding toward the distal end. Each also provides separate control lines for the different segments or groups. The control lines for the larger, proximal segments are more laterally spaced than those for the smaller, distal segments, which enables greater leverage to be applied to generate a proximal curve.

In Anderson and Iwatsuka the maximum limit of the curve available between adjacent segments (i.e., the minimum radius of curvature) is reached when the segments abut one another at contact points located at a lateral space from the center of the universal joint along the longitudinal axis. The universal joint defines a secure, if heavy, means for fixing the alignment of adjacent segments. This security of alignment, however, has the unfavorable result that when first applying tension to a control line, only the endmost segment attached to the control line, generally the closest proximal segment, becomes tilted relative to the next adjacent segment. This adjacent segment is not urged to tilt until the more proximal segment curves to reach the contact point defining its limit. With increasing tension, the curve of the arm as a whole begins with tilting of segments exclusively at the base or proximal area, and proceeds outwardly, segment by segment, as each of the segments in turn is curved to its limit.

It would be advantageous to provide a flexible positioning appendage which has good flexibility and bends in a continuous manner along its length, but which has sufficient structural integrity to support itself, plus a load on the free or distal end. The appendage should be controllably bendable at any area (or even individual joint) along its length, independent of curves at other areas. Preferably, this should be achieved in a device which defines a passageway for fluid or electrical lines and the like, and does not necessarily contract or elongate when tension is applied and released. Generally, it is desirable to provide for progressively greater stiffness and support proceeding towards the proximal end, however, a given application may require the capability of a pronounced bend at a certain point along the appendage. This is provided according to the invention by certain arrangements of resilient couplings and resilient segments, facilitating an appropriate selection of rigidity vs. flexibility which is apt for a number of applications as discussed in detail hereinafter.

SUMMARY OF THE INVENTION

It is an object of the invention to provide a low cost flexible positioning appendage which provides a maximum of flexibility and control with a minimum of structural complexity or weight.

It is another object of the invention to provide such an appendage which can be arranged when required to bend smoothly and continuously along its length, or to define preferential bend points which with increasing control line tension will tend to bend first.

It is also an object of the invention to provide a resilient coupling which spaces the segments in a flexible positioning appendage, but is not subject to variations in elongation as a result of tension applied to achieve position control.

It is a further object of the invention to provide a positioning appendage which is apt for a variety of diverse applications.

It is another object of the invention to provide a positioning appendage having a particular layout for the control lines which enables better operational control when the arm is cantilevered (i.e., extended substantially horizontally from a base).

It is still another object of the invention to enable the selection of structural parameters for segments and couplings between segments which can be chosen to enable either task-specific preferred bending points or generally equal bending along the length of the appendage.

It is a further object to provide a controllable appendage which can mimic the operation of animal appendages such as fingers, hands, elephant trunks, antennae, tails, tongues, etc., and are readily provided in the necessary size and shape to resemble such animal appendages, including the skeletal structures under the skin.

These and other objects are accomplished by a flexible appendage for use as a robot arm, controllable medical instrument, or simply a toy. The device has flexibly coupled segments preferably defining an open lumen, each segment having one or more flanges protruding laterally of a centerline or axis. The flanges have passages for control lines spaced laterally from the axis. Each control line is fixed at one end to a segment and can be pulled through the other segments from the other (proximal) end. With unequal tension, the control lines shorten a lateral side of the appendage to controllably bend the appendage as desired. Resilient couplings between the segments, leave open the lumen for passage of conduits or tools. The couplings can be helical springs wound with turns which abut at rest, such that the couplings can elongate on the outside of a bend (as the spring turns separate) but cannot compress on the inside of the bend, thereby maintaining a constant overall length of the appendage notwithstanding changes in control line tension. The control lines are distributed around the axis, and can be arranged in ranks for controlling groups of the segments at different distances from the proximal end. The springs coupling proximal segments can be more rigid than for distal segments, and the segments can be smaller and/or longitudinally shorter approaching the distal end.

BRIEF DESCRIPTION OF THE DRAWINGS

There are shown in the drawings exemplary embodiments of the invention as presently preferred. It should be understood that the invention is not limited to the precise arrangements and instrumentalities shown and discussed, and is capable of variation in accordance with the scope of the appended claims and their reasonable equivalents. In the drawings.

DETAILED DESCRIPTION OF THE PREFERRED EMBODIMENTS

Figure 1:
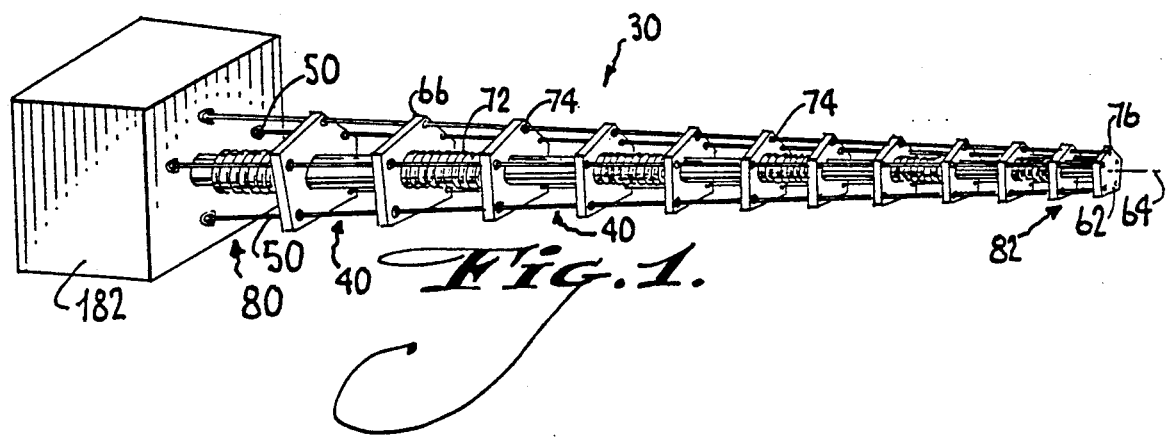
FIG. 1 is a perspective view illustrating a flexible positioning appendage in accordance with the invention, the appendage shown cantilevered from its base (i.e., extending horizontally)
Figure 2:
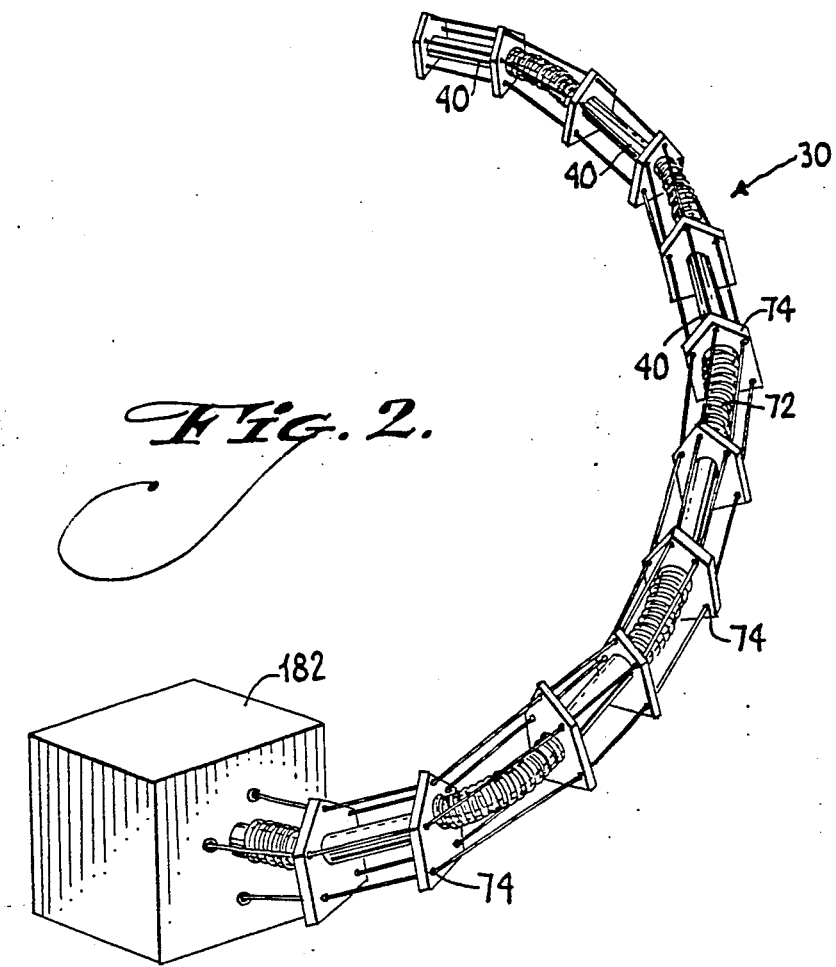
FIG. 2 is perspective view corresponding to FIG. 1, wherein the appendage is curved into a continuous arc.

As shown in a horizontal orientation in FIG. 1, and in an upwardly curved orientation in FIG. 2, the invention is a flexible positioning appendage or arm 30, comprising a plurality of resiliently coupled rigid segments 40 which can be pulled into a curve using control lines 50. Each of the segments 40 preferably defines an open lumen 62 along a longitudinal axis 64 of the appendage 30, and has at least one flange 66 protruding laterally of the axis. In the embodiment shown in FIGS. 1 and 2, each segment is a rigid element comprising two spaced flanges 66. Tubular resilient couplings 72 are disposed between each of the rigid segments 40, along the longitudinal axis and preferably aligned with the lumen of the segments.

The flanges 66 each have at least one passage 74 for receiving a control line 50. One end 76 of the control line is fixed to the flange of a segment closer to the distal end 82 of the appendage. The control line passes freely through the flange(s) of each of the segments between this more remote segment and the proximal end 80. Means are provided for applying tension to the control line 50. Provided the tension applied to the control line(s) is laterally unequal relative to the axis 64, the appendage 30 bends laterally toward the control line having the greater tension due to foreshortening of the lateral side of the appendage along which this control line passes. Whereas the coupling between the segments is resilient, the arm bends smoothly, accurately and continuously.

Depending on the task required, the appendage can be arranged to bend only in one direction (requiring only one control line), returning resiliently when tension is released. Preferably however, the segments 40 have a plurality of passages distributed around the axis 64, and the device comprises a plurality of control lines 50, whereby the appendage is bendable in opposed directions by tension on selected ones of the control lines.

Similarly, depending on the task required, the appendage can be arranged to have sections which vary in their susceptibility to bending. It may be desirable, for example, to have a relatively stiffer proximal section for general positioning and a relatively flexible distal section for fine positioning. Sections can be included which are not controllably bendable, and are either flexible or rigid. As one example, when attempting to fish an appendage of this type through branching conduits or the like, it may only be necessary to controllably bend the extreme distal end for guiding the appendage into a desired branch, after which it can be pushed. This can be accomplished by varying the dimensions and the flexibility of the joints between segments as well as the segments themselves.

A preferred means for varying flexibility is to vary the length of the spring or other resilient coupling between the segments. For example, shorter (stiffer) connections can be provided near the proximal end or base, and longer (more flexible) connections can be provided approaching the distal end, where greater flexibility and susceptibility to bending is desired. In the event a continuous length of spring is used along the appendage, the segments can be positioned at appropriately varying spacing along the spring, e.g., by screwing the segments along the helical pitch of the spring, and fixed in place.

The control lines can be arranged in ranks for controlling groups of the segments or even individual segments, at different distances from the proximal end 80. In that case at least one rank 92a (See FIG. 13) of control lines is fixed to a relatively more proximal segment than at least one other rank 92a (see FIG. 13) of control lines. In order to combat the tendency of the appendage to begin bending at the more proximal joints, the more proximal sections and/or the couplings between the more proximal sections can be made stiffer by being larger and heavier, and/or coupled by stiffer resilient couplings than the more distal sections. Another means for varying the bending proclivity of the joints along the appendage is to vary the lateral spacing between the axis and the point at which the control lines pass, a relatively more powerful bending force being produced by a relatively greater lateral spacing of the control lines.

In order to allow passage of conduits such as electrical wires, fluid lines, tools and the like, the central axis 64 of the segments 40 have an access opening, and the resilient couplings 72 between the segments are hollow. In a preferred embodiment, the couplings comprise helical springs 94, and the segments 40 each comprise a rigid tube 96 disposed along the axis and at least one flange plate aligned perpendicular to the tube. The springs 94 are coupled to the rigid tubes 96 of adjacent ones of the segments, either wrapping around the outer surface of the portion of tube 96 which protrudes beyond the flange plate, or being compressed into the lumen of the tube. Each segment 40 can have two flange plates, the rigid tube protruding from the flange plates at opposite ends of the segment with the spring wrapped thereon. In FIGS. 1 and 2 the segments 40 are of different lengths along the appendage or arm, at least some of the segments at a more proximal position along the arm having a greater spacing between the flange plates than segments at a more distal position. A variation in the stiffness of the resilient couplings can be achieved by using thicker spring wire, shorter axial spring lengths, etc., for the proximal couplings as compared to the distal ones. To increase stiffness, selected joints can have plural springs disposed inside one another, or a spring joint can be made stiffer by interposing another resilient material such as a length of rubber or plastic, or even a metal spring bar. In these ways, the bending proclivity along the appendage can be chosen as appropriate to the specific task of the appendage.

Figure 3:
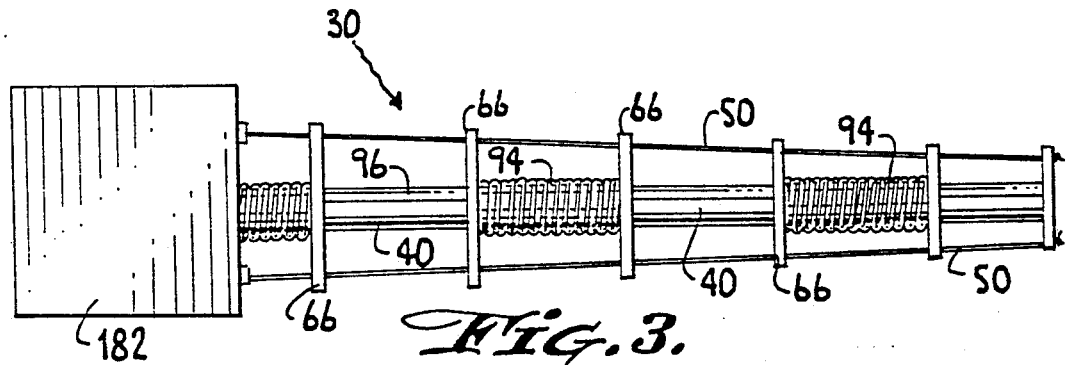
FIG. 3 is an elevation view showing a section along an embodiment of the invention having abutting-turn segment coupling springs.
Figure 4:
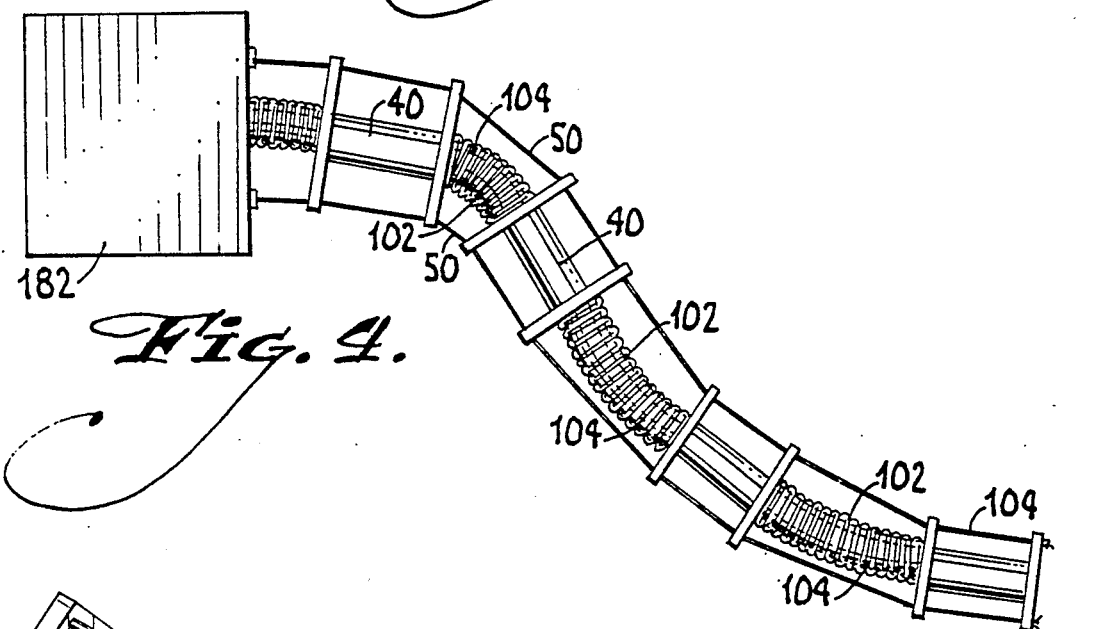
FIG. 4 is an elevation view corresponding to FIG. 3, with the section curved.

Helical springs are preferred where it is desirable to leave open the lumen. The helical springs 94 forming a resilient coupling between the segments preferably are so-called "closed" springs. The springs are wound such that adjacent turns of the springs rest against one another at rest. Accordingly, the adjacent turns 102 on a side of the appendage facing toward a bending radius remain in direct contact, defining a constant length regardless of changes in control line tension, while the turns 104 on the side of the appendage facing away from the bending radius separate, to allow bending. This aspect of the invention is illustrated in FIGS. 3 and 4. The same reference numerals have been used throughout the drawings to identify comparable parts in the respective embodiments of the inventions. When at rest (FIG. 3), the coils of the spring abut, and when curved (FIG. 4), the coils of the spring on the outside of the curve separate. However, whereas the coils on the inner side of the curve remain in abutment, the appendage as a whole is neither foreshortened by application of tension to the control lines, nor elongated upon release of tension. This feature improves control of the position of the distal end 82 of the appendage, which for example can hold a tool.

Figure 5:
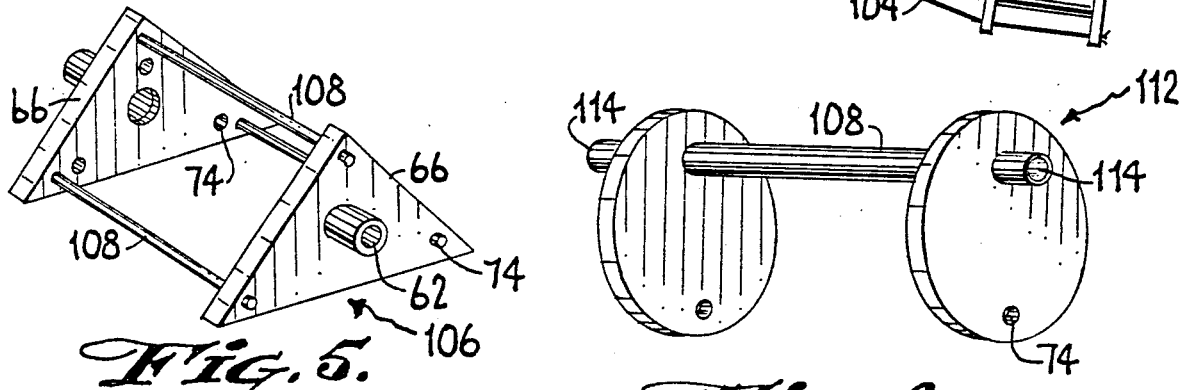
FIGS. 5 through 7 are perspective illustrations showing some alternative segment structures.
Figure 6:
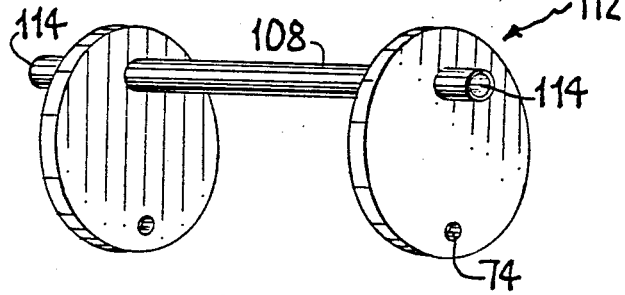
Figure 7:
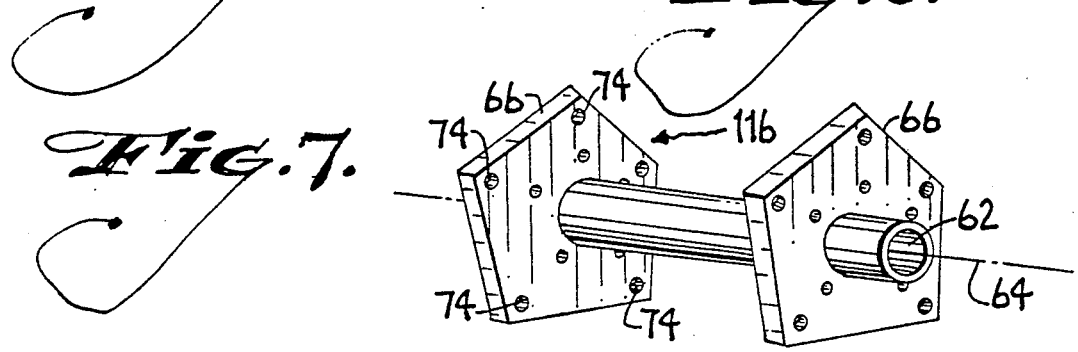

FIGS. 5–7 illustrate some alternative forms of segments. The illustrated segments in each case comprise two spaced flange plates 66, carried on a rigid spacing structure such as a tube, brace or series of braces, whereby each segment is a rigid element. The segments can be made, for example of polycarbonate or a similar relatively rigid material. The segments can also be defined by other shapes, provided a passage for a control line spaced laterally of the axis is provided. One possible segment is a simple tube or cylinder having grooves or holes spaced laterally from the center and running parallel to the axis for carrying the control lines. It is also possible to make the segments themselves resilient, e.g., by use of a flexible material to space the flanges. A more flexible segment or joint results in an overall more sinuous and flexible arm, at the expense of accuracy of positioning control. A smaller segment, especially a short segment only a single flange, provides relatively greater flexibility than a larger one with spaced flanges, due to the fact that more springs are required over a given length for smaller segments than larger ones, and retains good accuracy of control.

The triangular flange plate segment 106 in FIG. 5 is provided with three passages 74 for control lines 50, and a central opening 62. Instead of a tube for spacing the flange plates, a rigid segment structure is provided by braces 108 at the apices of the flange plates, associated with each of the control line passages 74. This arrangement is useful in particular for the segment which forms the distal terminus of the control lines, since the longitudinal tension on the control line tending to pull the segment into a curved orientation is resisted in each case by an associated brace 108. Preferably, the terminus of the control lines is on the distal-side flange 66 of the respective segment, but the terminus could also be on the proximal side or at an intermediate point.

FIG. 6 illustrates a segment 112 arranged to bend in only one direction. In this segment the brace 108 between the flange plates can be a solid member or a hollow one, e.g., a tube. The helical spring for coupling the segments (not shown in FIG. 6) can be wrapped over the protruding end 114 of the brace 108. Whereas the passage 74 for the control line is laterally spaced from the coupling defined by the spring and the brace, an arm 30 using this form of segment bends toward the control line when tension is applied, or straightens to a point defined by the connecting springs 94 when tension is released. This form of segment is advantageous in connection with an application such as the movable-mandible mask shown in FIGS. 9 and 10.

In an embodiment with a single control line, the springs provide the means for recovering when tension is released. By using shorter and thicker springs, the recovery can be positive. The springs can be arranged to return the appendage to a straight line or a curved line, either in the same direction as the bend or in the opposite direction, past the centerline.

FIG. 7 illustrates a particular arrangement of the holes 74 provided for passage of the control lines. This form of segment is particularly useful where the appendage is cantilevered, or oriented substantially horizontally, requiring tension on the upper control lines simply to hold the appendage against drooping under the influence of gravity. Assuming the flange is a regular pentagon as shown, the uppermost control line is centered over the axis 64. The side lateral control lines and the lower control lines are placed slightly higher than the respective line between the axis 64 and the corresponding apex of the pentagon. Accordingly, the pattern of control lines is shifted vertically relative to the axis 64, giving the operator additional mechanical advantage in overcoming the tendency of the appendage to droop. Of course, a vertically shifted pattern can also be provided on other flange shapes than pentagons, e.g., round, square, triangular, etc.

In FIG. 7, not only is the pattern of control lines shifted vertically, but the passages are not equally distributed. More of the control lines are disposed above the longitudinal axis 64 (specifically three control lines) than below it (two). This also makes it easier to control the horizontally oriented arm. In a suitably resilient arm it may be possible to eliminate all the control lines below the axis 64, allowing gravity to bend the arm downwardly when needed.

Of course, in many instances the appendage need not be cantilevered and a symmetrical arrangement of the control wires is appropriate. The invention may be particularly useful, for example, as a manipulating tool in a zero gravity space environment or underwater, where gravity is less of a problem.

Figure 8:
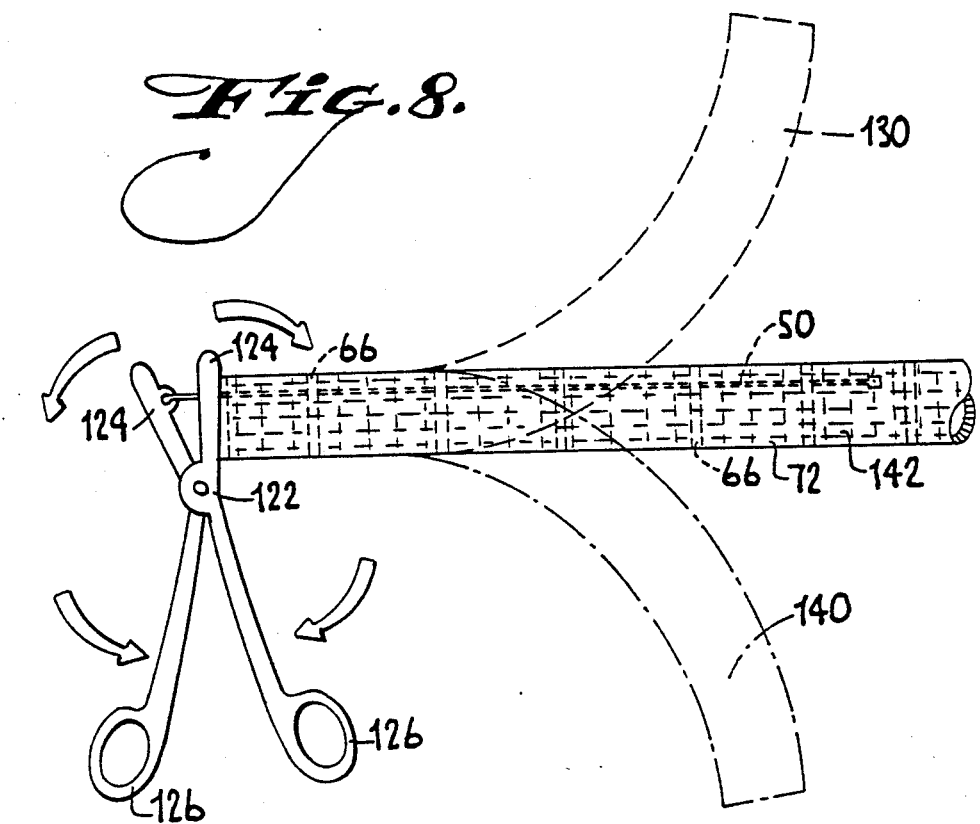
FIG. 8 is an elevation view illustrating application of the invention to a device for positioning a medical instrument.

At least three control lines are needed to enable curving of the appendage in any selected direction. However, curvature in one direction or in limited directions may be adequate in many instances. For example, where the capability exists to rotate the arm around its longitudinal axis, bending in one plane would enable positioning of the distal end at any point within a substantially spherical envelope. FIG. 8 illustrates the application of the invention to a form of medical instrument 120 under such circumstances. The arm 30 in this case provides a steerable conduit, for example to admit an endoscope or laparoscope, which enables the operator to curve the distal end 82 to reorient a viewing apparatus or to steer the arm for advance through a body passage. Whereas the operator can release tension and rotate the arm, curvature in one direction is adequate in this case. Of course it is also possible to provide for controlled curvature in two opposed directions or in any direction, by use of the required number of control lines 50.

In FIG. 8, a pivoting handheld tool 122 is coupled to the proximal end 80 of the arm 30 by one of two tip portions 124, and the control line 50 is coupled to the other. By manually bringing together the finger grips 126 of the tool, the tip portions 124 are forced apart, thus exerting tension on the control line 50. The control line passes freely through the segments of the arm to an attachment at a segment near the distal end. The arm can be arranged to curve from a straight orientation as shown in solid lines, to a curved orientation 130, shown in dashed lines. Alternatively, the rest position can be curved opposite the direction of curvature, as shown in dash-dot lines 140, enabling the arm to be oriented as required in two opposite directions, while only requiring one control line 50.

The embodiment according to FIG. 8 can be arranged with a plurality of relatively more rigid segments 40 separated by relatively more flexible tube sections 72. The control line can run along a groove in the outer edge of the segments, or through passages spaced from the edge. A flexible sheath 142 is preferably provided on the outside of the arrangement, with means provided to allow the control line to move under the flexible sheath.

Figure 9:
FIG. 9 is a perspective view illustrating application of the invention to a toy monster mask having movable mandible structures.
Figure 10:
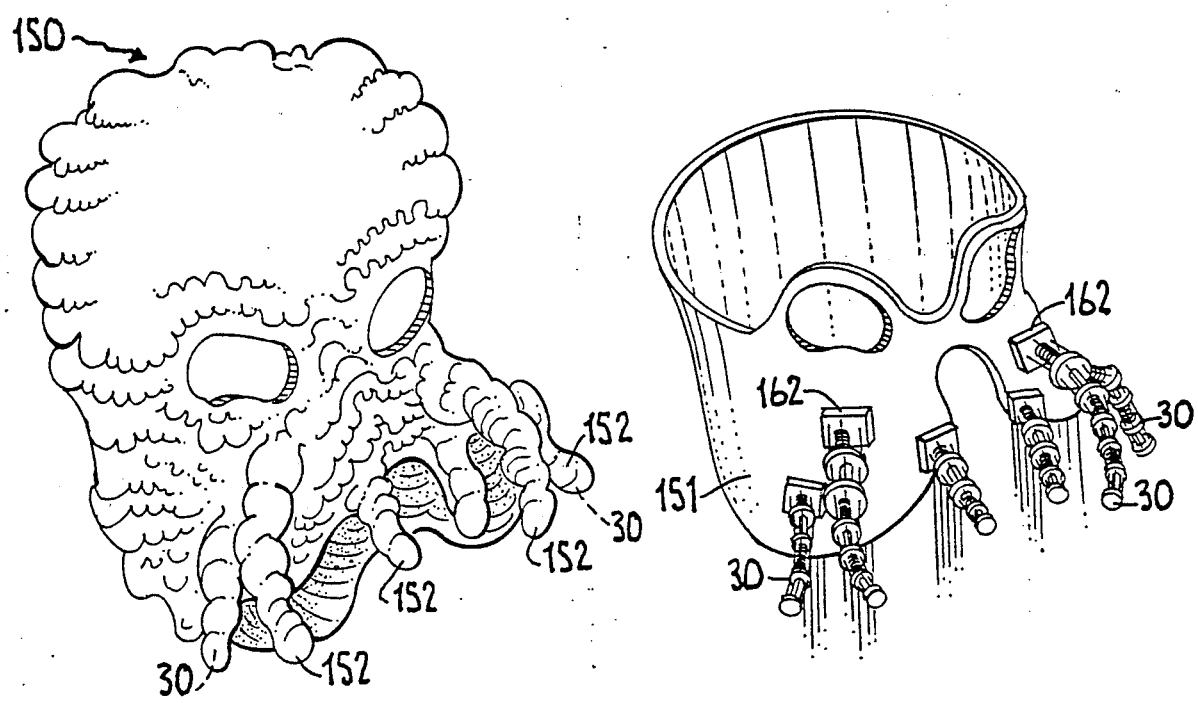
FIG. 10 is an elevation view, partly in section, showing a means for driving the appendages provided in the mask of FIG. 9.
Figure 10:

In FIG. 9, a plurality of appendages 30 are provided on a mask 150, for simulating movable mouth parts 152 on an alien or humanoid monster. The mask is made of an elastomeric skin material disposed on a frame as shown in FIG. 10, including a number of movable appendages 30 according to the invention, which can be controllably curved, e.g., inwardly toward the mouth, by application of tension to respective control lines, or released to a rest position upon release of tension. The control lines can be run through the material of the mask, for example in embedded guide tubes, to a convenient location for the application of tension. Guide tubes such as Bowden wire tubes can be attached adhesively to the mask, for routing the control lines to a suitable control location. A structure can be provided, for example, to exert tension on the lines when the wearer flexes his or her jaw behind the mask. Alternatively, an electromagnetic actuator is possible, or the control lines may be coupled by a Bowden wire arrangement to a handheld caliper-like manual controller.

The underlying structure 151, as shown in FIG. 10, forms a relatively rigid base. The respective appendages 30 have proximal segments 162 which are attached to rigid mask structure 151, with the control lines routed through structure 151 to the interior. Each of the appendages can have one control line, using segments substantially as shown in FIG. 6, coupled by open helical springs. The segments are arranged such that when tension is applied, the appendages foreshorten and curve inwardly as if pulling toward the mouth area. Upon releasing tension, the appendages return to a rest position defined by the springs, which can be straight or curved. A plurality of control lines can also be used, for more extensive positioning control.

This is but one example of the use of the invention for simulation of the appendages of living things. Other possibilities include the trunk of an elephant, the tentacle of an octopus, fingers, hands, antennae, tails, tongues, etc. The appendage is such that by applying a skin-like surface material or sock over segments dimensioned to approximate the skeletal members of a human or animal, a convincing mimicry is achieved. This mimicry is especially effective in connection with sinuous shapes, but can also apply to more jointed human and animal parts.

Figure 11:
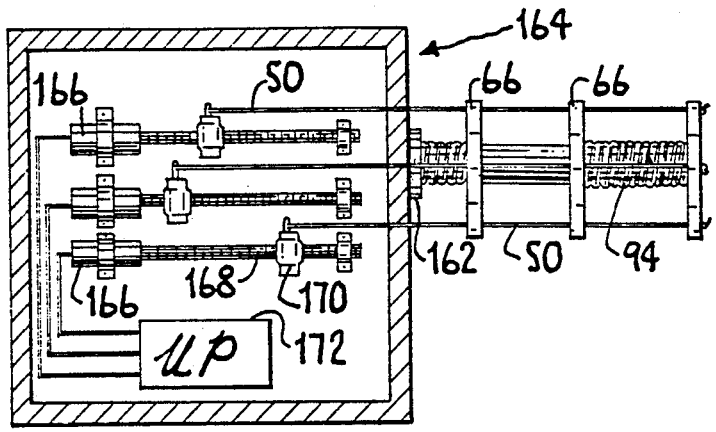
FIG. 11 is a section view through an electrically driven embodiment including a controller.

FIG. 11 illustrates one alternative for an automated and/or electromechanically driven arrangement. In this embodiment three control lines pass from a proximal segment 162 mounted rigidly on a drive box 164, to motors and controls mounted inside. Each control line has a motor 166 for rotating a threaded shaft 168 carrying a nut 170 to which the respective control lines 50 are attached. The three control lines are independently positionable in this manner, and assuming the three lines are distributed around the axis of the arm, the arm can be curved in any direction. A microprocessor controller 172 is coupled to drive the motors via suitable drivers. The motors preferably are stepping motors and/or are geared for accurate displacement of the control lines over small spans for setting the distal end 82 to predetermined positions, which can be stored in the microprocessor memory. Limit switches (not shown) can be provided to reference each movable nut to a zero point. Alternatively, a reference position of the arm 30 can be defined by manually controlling the arm to place the distal end at a predetermined point, and subsequent movements made relative to the reference position.

Other forms of drive unit are also possible. For example, motors rotating spools or crank arms to which the control lines are attached is another possibility. The drive can also employ pneumatic or hydraulic cylinders for applying tension to the control lines, etc.

Figure 13:
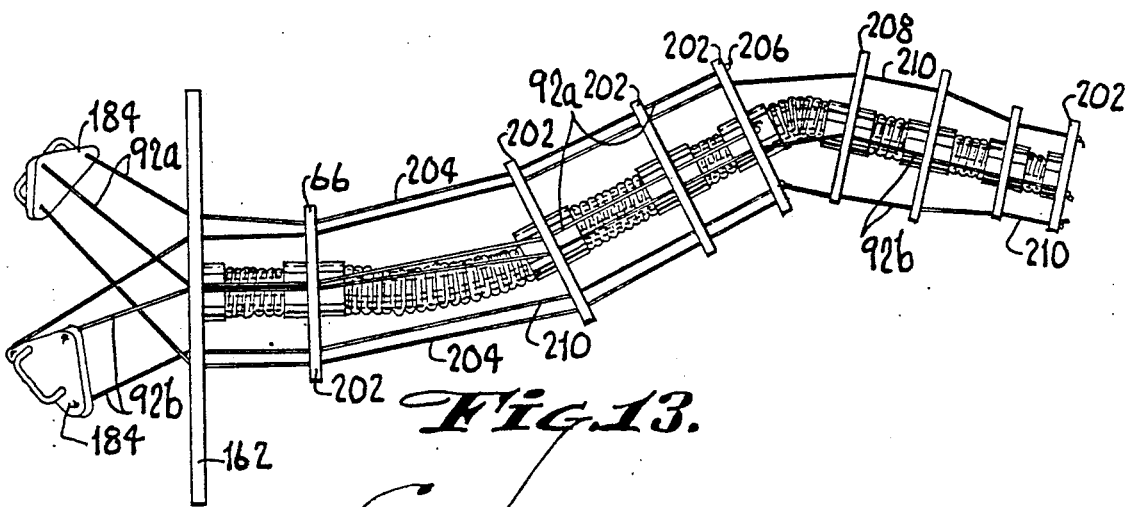
FIG. 13 is an elevation view illustrating ranked control lines operable independently to bend different subsections along the longitudinal axis.

The invention is also applicable for manual drive, and makes an interesting toy. The proximal segment is mounted to a base 182 which can be securely positioned against tension exerted by the operator on the control lines 50. The base can be adapted to be sat upon or knelt upon by the user. The control lines are preferably attached at spaced points on one or two control handles 184 as shown in FIG. 13. By pulling on the control handle while canting the control handle relative to the base 182, unequal tension is exerted on the control lines, and the arm is curved in any direction selected as a function of the specific cant of the handle relative to the base.

Figure 12:
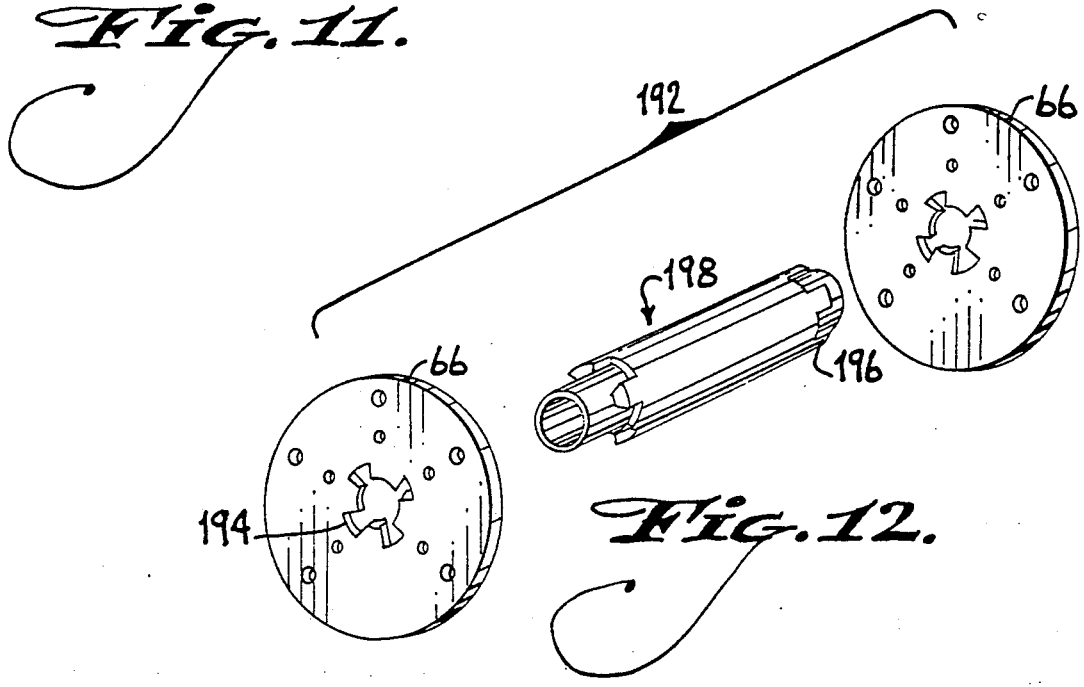
FIG. 12 is an exploded perspective view illustrating a preferred segment structure for a pentagonal arrangement of ranked control lines.

FIG. 12 shows another form of segment 192, which comprises easily assembled and disassembled parts, which makes this version useful in connection with a toy. The flange plates have central holes including a locking structure such as a dovetail mortise 194, mating with complementary structures 196 on the tube 198 which spaces the flange plates. A snap fit is preferred, whereby the device can be assembled by the user. As in FIG. 7, the flange plates according to this embodiment have passages for ranked control lines, offset vertically from positions at which the control lines would be equiangular around the center axis. Segments of this type can be attached using flexible connectors such as springs.

FIG. 13 illustrates an embodiment wherein the control lines are ranked. The more proximal segments 202 are relatively larger in diameter and are coupled by relatively stiffer and/or shorter springs. These segments are controlled using one set 204 of three or more control lines, which terminate at a distal one 206 of the larger segments. The remaining segments 208 proceeding to the distal end 82 of the arm, are smaller and coupled by relatively more flexible springs. The distal segments 208 are independently controlled using a group 210 of three or more control lines. This arrangement provides strength and control in the proximal section, for carrying and grossly positioning the arm, as well as dexterity in the distal section. Preferably, the ranked segment arrangement is used together with a variation in the stiffness of the resilient couplings, the more proximal rank of segments being more stiffly coupled than the distal rank of segments. This variation can be achieved by using heavier and/or axially shorter springs in the proximal rank than in the distal rank.

The control lines 210 for the distal segments 208 are disposed radially inwardly toward the axis, and those 204 for the proximal sections 202 are disposed radially outwardly from the axis, the control lines running parallel. Attaching the proximal control lines on the outside provides additional leverage in positioning the arm by application of tension. In a manual version of this embodiment, each set of control lines can be attached to a handle 184 which can be pulled and/or tilted relative to the base and the fixed proximal segment 162, for exerting unequal tension. Whereas the ranked controls are independently operable, the arm of FIG. 12 can be formed into a compound bend, with the proximal rank bent in one direction and the distal rank in another direction.

With a manually operated arm, the controls are generally limited to two ranks, operable with a control handle for each or the user's hands. An automated control advantageously can have a larger number of ranks. The control lines for the more proximal ranks are arranged along the outer portions of the proximal flange plates, with the more distal ranks placed radially inward, running through the proximal segments to their respective connections of segments located closer to the distal end of the arm.

The invention is subject to wide variations. For example, although the proximal segments are generally larger, not all the segments need be of the same length and it is possible that using longer distal segments may be appropriate for some applications, such as spray painting, wherein a sweeping distal motion may be needed to move a spray head over a path. Additionally, the invention can be applied to intermediate joints or elbows, as well as to the distal end of an automated appendage. The invention is also apt for a wide variety of specific applications, only a few examples being discussed herein.

Figure 14:
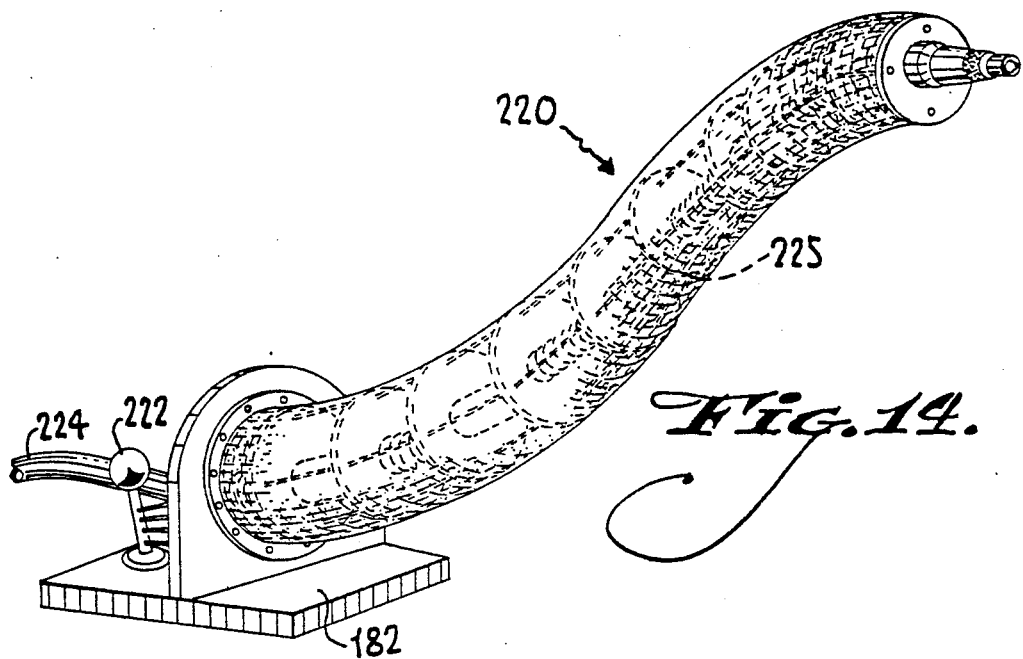
FIG. 14 is a perspective view of an embodiment having a skin structure disposed over segments, arranged for controlling the aim of a garden hose.
Figure 15:
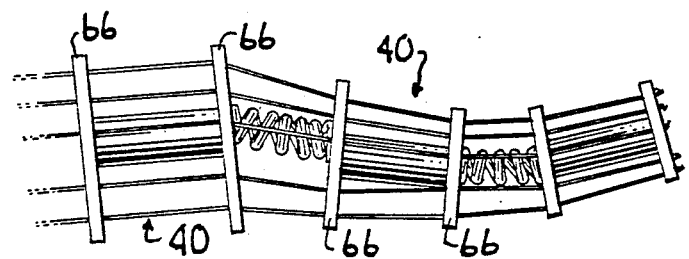
FIG. 15 is a partial elevation view showing joints formed with open springs, rendering the appendage longitudinally compressible.

FIG. 14 illustrates application of the invention to a toy 220 used for aiming a garden hose 224. A joystick-like manual control 222 is coupled to the base 182 of the device for operating the control lines. The segments, shown in phantom lines, are progressively smaller leading to the free end, and are connected by springs leaving a lumen of sufficient size to receive the garden hose 224. The appendage portion of the toy is covered by a sock or similar skin 225, stretched over the segments. Alternatively, the segments can be potted in a soft foam plastic or the like. Whereas critical positioning is absolutely necessary in a garden hose aiming toy, the springs can be open springs as shown in FIG. 15, or closed springs as shown in FIG. 16.

Figure 16:
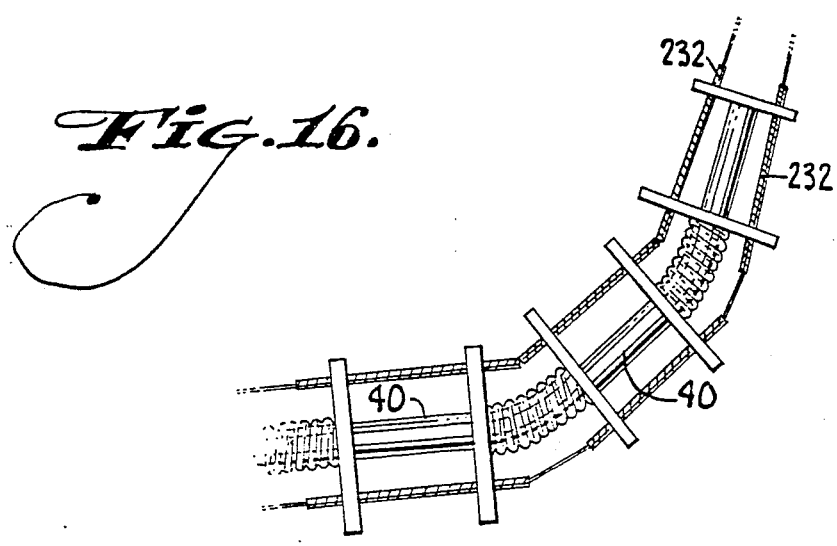
FIG. 16 is a partial elevation view wherein the bending radius is limited by control wire sheaths in a Bowden cable like arrangement.
Figure 17:
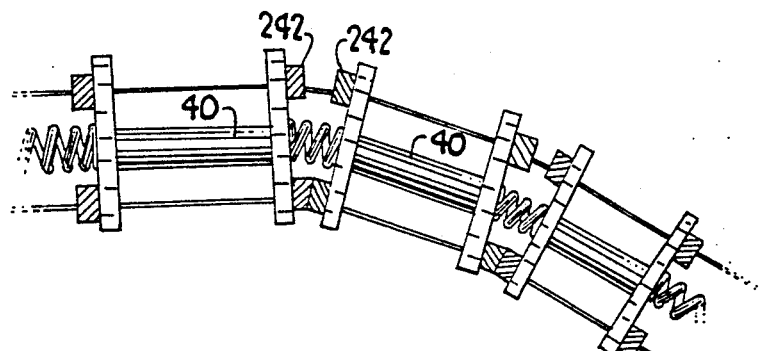
FIG. 17 is a partial elevation view wherein the bending radius is limited by protrusions of the segments.

FIG. 16 illustrates an embodiment wherein the control lines are carried in sheaths 232 extending through the segments 40, or at least protruding from the ends of the segments. The sheaths 232 preferably are flexible and attached to the segment flanges by adhesive, being of a material similar to bicycle brake cable sheathing. The sheaths 232 have the further aspect of limiting the minimum bending radius which can be achieve by tension on the control lines. As shown in FIG. 16, when the appendage is curved to the point that the sheaths 232 of adjacent segments on the inside of the curve come into abutment, the appendage cannot be curved further. FIG. 17 achieves a similar limitation on the minimum bending radius by means of spacers 242 provided on the ends of the segments, which contact the adjacent segment to define the minimum radius. The segments can have such spacers on one side only, or on both sides as shown.

Figure 18:
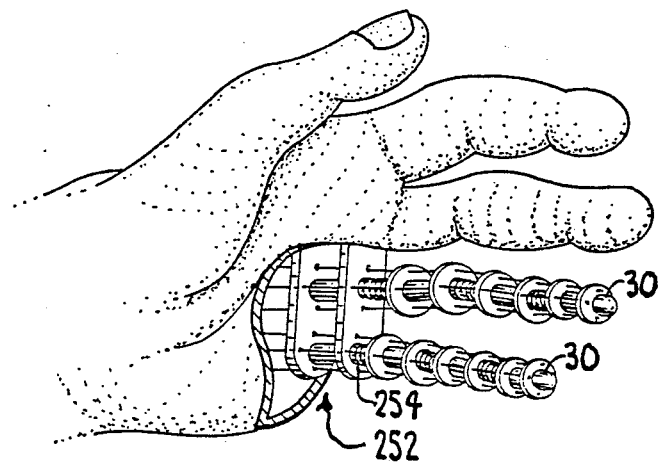
FIG. 18 is a partial cutaway view showing application of the segments to simulate a human hand, including a metacarpal area wherein a plurality of the distallyseparate appendages (phalanges) are joined so as to be bendable as a unit.

FIG. 18 is an example of an arrangement wherein the control lines are ranked, but the different ranks are materially different forms of appendage. FIG. 18 is a partial cutaway view showing application of the invention to simulate a human hand. The fingers are simulated by separate appendages 30 substantially as discussed above. The segments can be dimensioned similarly to the finger bones of the human hand, thus simulating the knuckles in the fingers or phalanges. In the metacarpal area 252 (i.e., in the palm portion of the hand), the separate phalange appendages are joined at a one or more proximal ranks so as to be bendable in at least one plane as a unit, thus simulating natural grasping motions. Four fingers can be mounted on metacarpal segments 254, or pairs of two fingers can be mounted on metacarpal segments in a similar manner. Of course it is also possible to extend the series of segments 30 separately from the phalanges to the carpus, as characteristic of the bones of human hands. Preferably, the metacarpal segments 254, whether separate or joined as shown, are operably via a separate rank of control lines, thus enabling the fingers to be flexed or extended without also bending across the palm, and vice versa.

Figure 19:
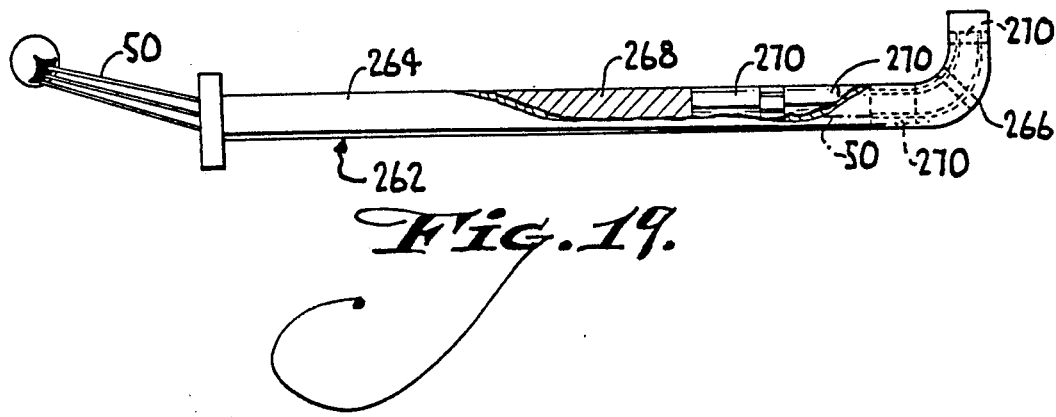
FIG. 19 is a partially cut away elevation view showing an alternative form of medical instrument having a preferential distal bending area; and, FIG. 20 is a perspective view of a boxing toy.

FIG. 19 is a partially cut away elevation view showing an alternative form of medical instrument 262 having a preferential distal bending area 266. This instrument is provided with a less flexible or less controllable proximal section 264 and a very flexible extreme distal end 266, for guiding the instrument. The instrument is useful for procedures such as bronchial suctioning, wherein it is necessary to guide a suction apparatus through branching bronchial passages. The user can readily select between passages at a branch by diverting the distal end 266 of the instrument using unequal control line tension.

The instrument of FIG. 19 is preferably constructed of a substantially continuous flexible plastic, having segments 270 embedded in a plastic body 268 during molding. The segments, shown in dotted lines in FIG. 19, are more closely spaced at the less flexible proximal end 264, and less closely spaced at the distal end 266, where preferential bending is desired.

Figure 20:
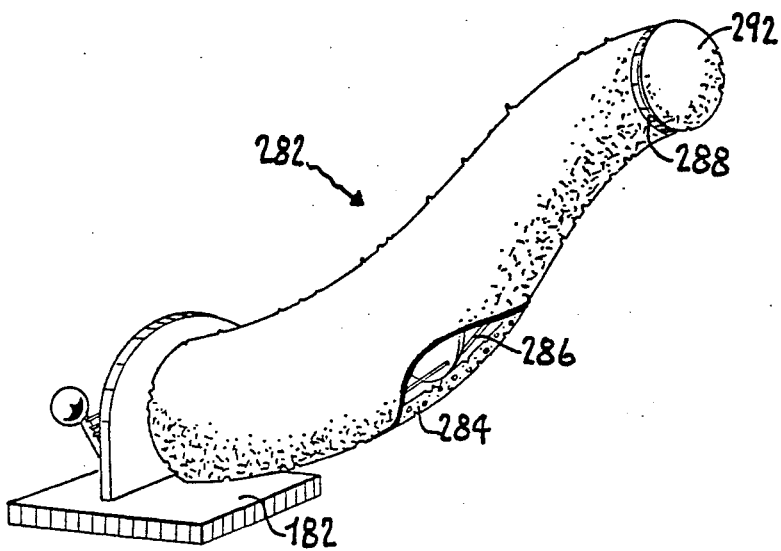

FIG. 20 illustrates another embodiment of a toy 282. In this arrangement the appendage comprises a continuous body 284 of soft plastic such as foamed polyurethane. The control lines extend through openings running along the length of the appendage, which may be strengthened by compressible guide tubes 286 or by spaced lengths of non-compressible guide tubing. Paths for the control lines can be formed by displacing the control lines in the potting material before it has fully set, to disengage the control lines from the potting and/or to enlarge the openings for the control lines. A rigid segment plate 288 is provided near the distal end for attachment of the control lines. A soft bulb 292 covers the rigid distal segment plate 288, to avoid injury. This toy is a form of soft boxing toy, intended to allow two participants to assume closely facing positions and to control their respective soft appendages to strike at one another.

The invention having been disclosed, additional variations will become apparent to persons skilled in the art. The invention is intended to cover not only the exemplary arrangements discussed herein, but also a reasonable range of equivalents. Reference should be made to the appended claims rather than the foregoing examples, in order to assess the scope of the invention in which exclusive rights are claimed.

I claim:

1. A flexible positioning appendage, comprising:
   a plurality of segments, aligned to define a longitudinal axis of the appendage, each of the segments having at least one opening spaced laterally of the axis, defining a passage substantially parallel to the longitudinal axis;
   resilient couplings spacing the segments; and,
   at least one control line having an end fixed to a remote one of the segments, spaced from a proximal end of the appendage, the control line passing through the passage of each of the segments between the remote segment and the proximal end, whereby tension on the control line causes the appendage to bend laterally toward the control line;

wherein each of the segments defines an open lumen substantially along the longitudinal axis, and wherein the resilient couplings are hollow tubular structures, aligned with the lumen of the segments; and, wherein the tubular resilient couplings between respective ones of the segments have different rigidities.

2. The flexible positioning appendage according to claim 1, wherein the segments have a plurality of passages distributed around the axis, and further comprising a plurality of control lines, whereby the appendage is bendable in opposed directions by tension on selected ones of the control lines.

3. The flexible positioning appendage according to claim 2, wherein the control lines are arranged in ranks for controlling groups of the segments at different distances from the proximal end, at least one rank of control lines being fixed to a relatively more proximal segment than at least one other rank of control lines.

4. The flexible positioning appendage according to claim 3, wherein at least one of said ranks of segments is joined to a plurality of separated appendages defining a next successive rank.

5. The flexible positioning appendage according to claim 1, wherein at least one of dimensions of the segments and flexibility characteristics of the resilient couplings vary along the appendage to form at least one area of preferential bending.

6. The flexible positioning appendage according to claim 5, wherein the area of preferential bending is at a distal end of the appendage.

7. The flexible positioning appendage according to claim 1, further comprising a surface material disposed over the segments.

8. The flexible positioning appendage according to claim 1, further comprising means for limiting a minimum bending radius between adjacent segments including at least one of a sheath on a control line extending through at least a portion of a segment and a spacer protruding between adjacent segments.

9. The flexible positioning appendage according to claim 1, further comprising sheaths enclosing the control lines over at least a portion of the appendage, and wherein the sheaths are one of compressible and gapped, for allowing foreshortening of a lateral side of the appendage to achieve bending.

10. A flexible positioning appendage, comprising:
a plurality of segments, aligned to define a longitudinal axis of the appendage, each of the segments having at least one opening spaced laterally of the axis, defining a passage substantially parallel to the longitudinal axis;
resilient couplings spacing the segments; and,
at least one control line having an end fixed to a remote one of the segments, spaced from a proximal end of the appendage, the control line passing through the passage of each of the segments between the remote segment and the proximal end, whereby tension on the control line causes the appendage to bend laterally toward the control line;

wherein each of the segments defines an open lumen substantially along the longitudinal axis, and wherein the resilient couplings are hollow tubular structures, aligned with the lumen of the segments;

wherein each one of the segments comprises a tube disposed along the axis and at least one flange plate aligned perpendicular to the tube, the resilient tubular couplings being coupled to the tube of adjacent ones of the segments; and, wherein each segment has two flange plates, the tube protruding from the flange plates at opposite ends of the segment.

11. The flexible positioning appendage according to claim 10, wherein the tubular resilient couplings comprise helical springs.

12. The flexible positioning appendage according to claim 10, wherein the segments are of different lengths along the appendage, at least some of the segments at a more proximal position along the appendage having a greater spacing between the flange plates than segments at a more distal position.

13. A flexible positioning appendage, comprising:
a plurality of segments, aligned to define a longitudinal axis of the appendage, each of the segments having at least one opening spaced laterally of the axis, defining a passage substantially parallel to the lnogitudinal axis;
resilient couplings spacing the segments; and,
at least one control line having an end fixed to a remote one of the segments, spaced from a proximal end of the appendage, the control line passing through the passage of each of the segments between the remote segment and the proximal end, whereby tension on the control line causes the appendage to bend laterally toward the control line; and,
wherein each of said segments comprises axially spaced flanges, coupled together to form a rigid segment structure.

14. A flexible positioning appendage, comprising:
a plurality of segments, aligned to define a longitudinal axis of the appendage, each of the segments having at least one opening space laterally of the axis, defining a passage substantially parallel to the longitudinal axis;
resilient couplings spacing the segments; and,
at least one control line having an end fixed to a remote one of the segments, spaced from a proximal end of the appendage, the control line passing through the passage of each of the segments between the remote segment and the proximal end, whereby tension on the control line causes the appendage to bend laterally toward the control line;
wherein each of the segments defines an open lumen substantially along the longitudinal axis, and wherein the resilient couplings are hollow tubular structures, aligned with the lumen of the segments;
wherein the tubular resilient couplings comprise helical springs; and,
wherein at least some of the helical springs are wound such that adjacent turns of springs rest against one another at rest, the adjacent turns resting against one another on a side of the appendage facing toward a bending radius, defining a constant length, and separating on a side of the appendage facing away from the bending radius, to allow bending.

15. The flexible positioning appendage according to claim 14, wherein each of the segments comprises a tube disposed along the axis and at least one flange plate aligned perpendicular to the tube, the springs being coupled to the tubes of adjacent ones of the segments.

16. The flexible positioning apparatus according to claim 14, wherein the segments comprise axially spaced flanges, coupled to permit at least some tilting of the flanges.

17. The flexible positioning appendage according to claim 14, further comprising a potting material molded over the segments.

* * * * *